United States Patent [19]

Engelbrecht et al.

[11] Patent Number: 5,413,607
[45] Date of Patent: May 9, 1995

[54] KNEE JOINT PROSTHESIS

[75] Inventors: Eckart Engelbrecht, Hamburg; Elmar Nieder, Jork, both of Germany

[73] Assignee: GMT Gesellschaft fur Medizinische Technik mbH, Hamburg, Germany

[21] Appl. No.: 117,437

[22] Filed: Sep. 7, 1993

Related U.S. Application Data

[63] Continuation of Ser. No. 800,327, Nov. 29, 1991, abandoned.

[30] Foreign Application Priority Data

Nov. 29, 1990 [DE] Germany .................. 40 38 037

[51] Int. Cl.⁶ ............................................. A61F 2/38
[52] U.S. Cl. .................................. 623/20; 623/18
[58] Field of Search ............................. 623/20, 18

[56] References Cited

U.S. PATENT DOCUMENTS

| | | | |
|---|---|---|---|
| 3,696,446 | 10/1972 | Bousquet et al. | 623/20 |
| 4,262,368 | 4/1981 | Lacey | 623/20 |
| 4,301,553 | 11/1981 | Noiles | 623/20 |
| 4,888,021 | 12/1989 | Forte et al. | 623/20 |
| 4,938,769 | 7/1990 | Shaw | 623/20 |

Primary Examiner—David H. Willse
Attorney, Agent, or Firm—Darby & Darby

[57] ABSTRACT

A knee joint prosthesis with a tibial component, a femoral component and a hinge which connects the two components and defines a pivot axis at a fixed distance from both components. The planes of the axes of shanks of the two components are located at selected distances from each other and from the pivot axis, and the pivot axis is placed nearer to the rear portions than to the front portions of the two components. This reduces the need for resection of affected bones and enhances the transfer of forces as well as the stability of the prosthesis.

72 Claims, 6 Drawing Sheets

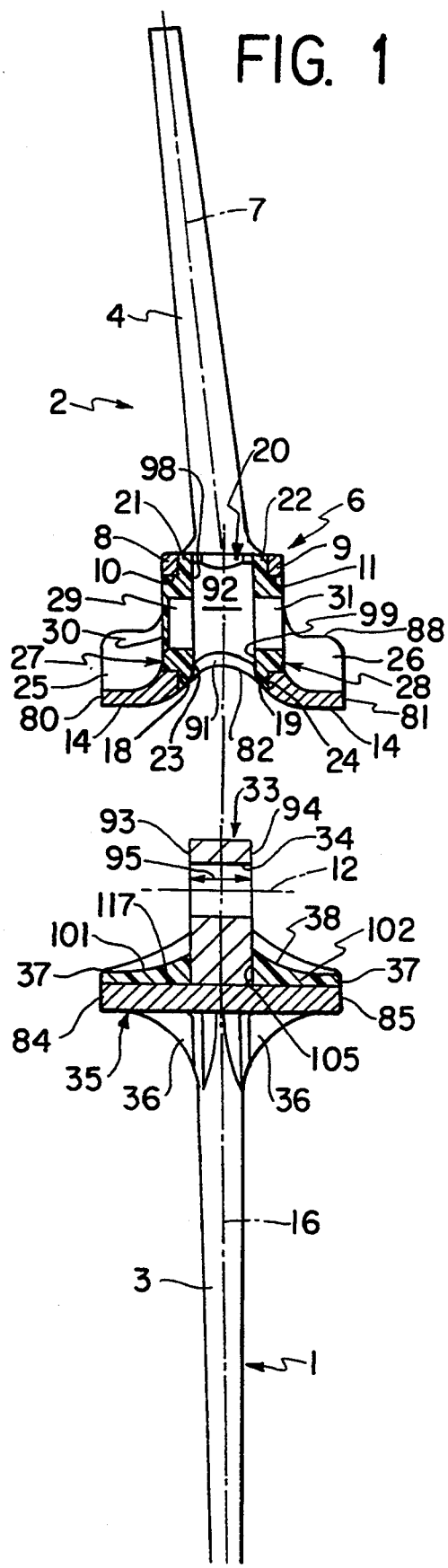
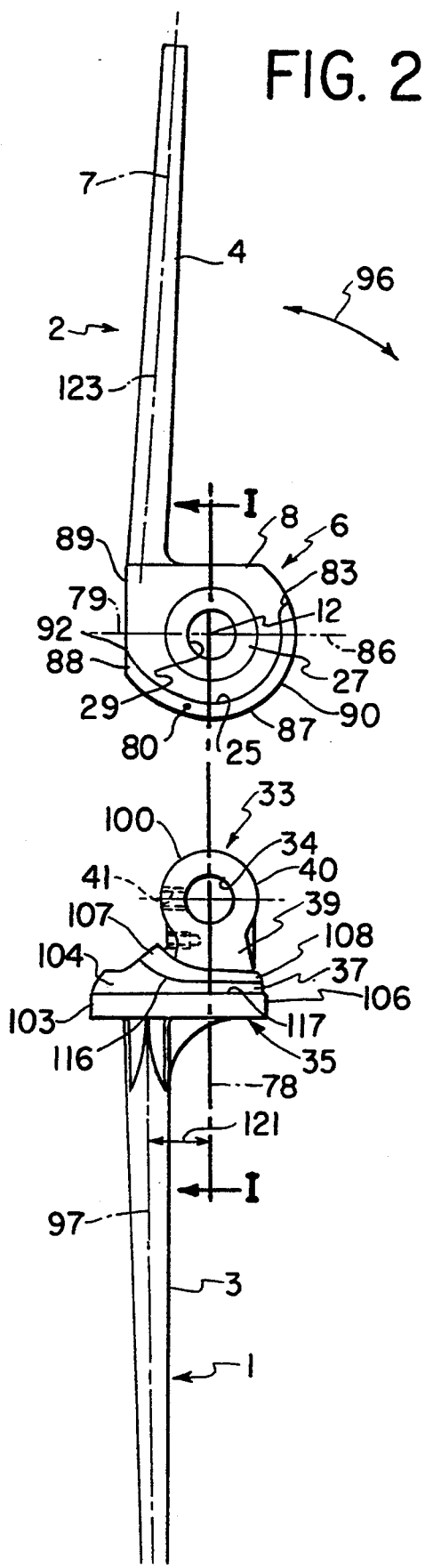

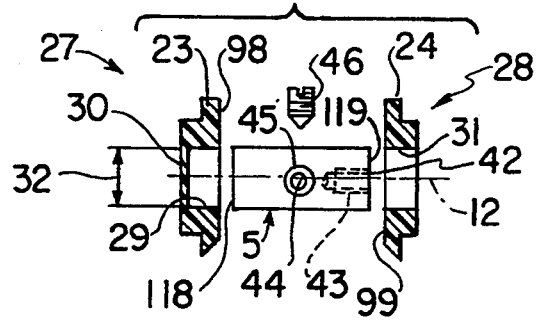
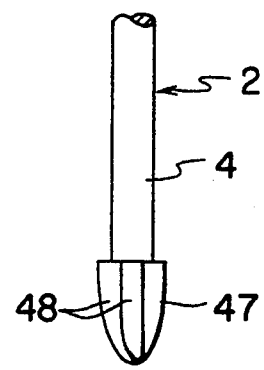
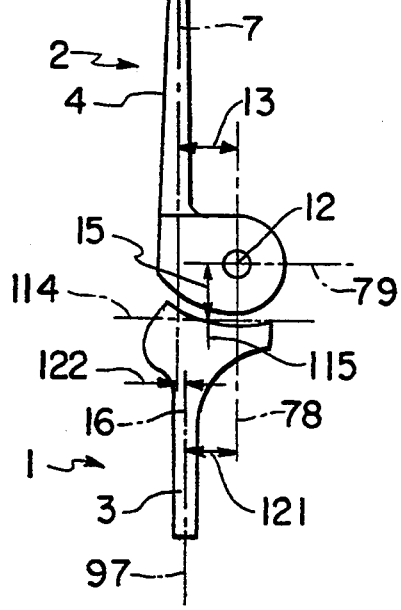
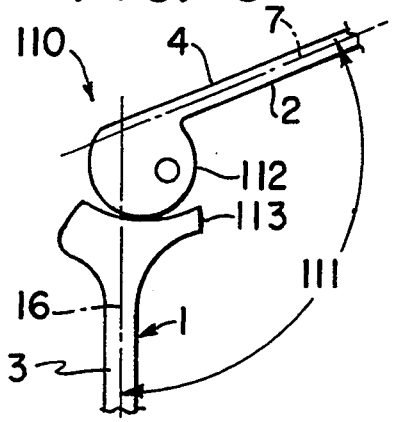
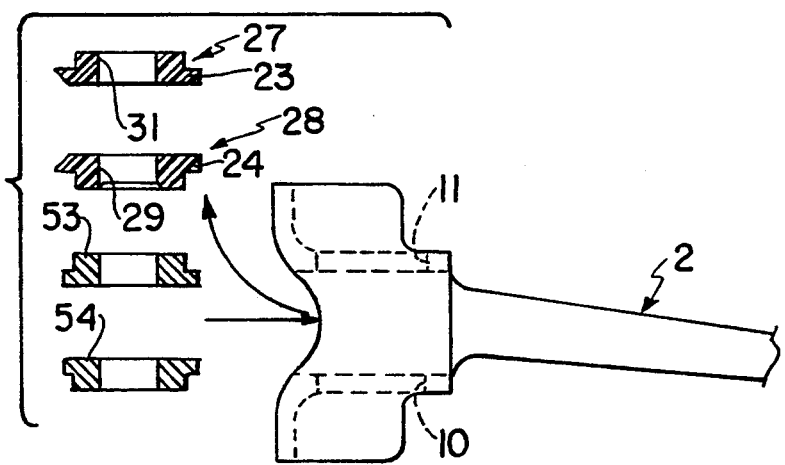

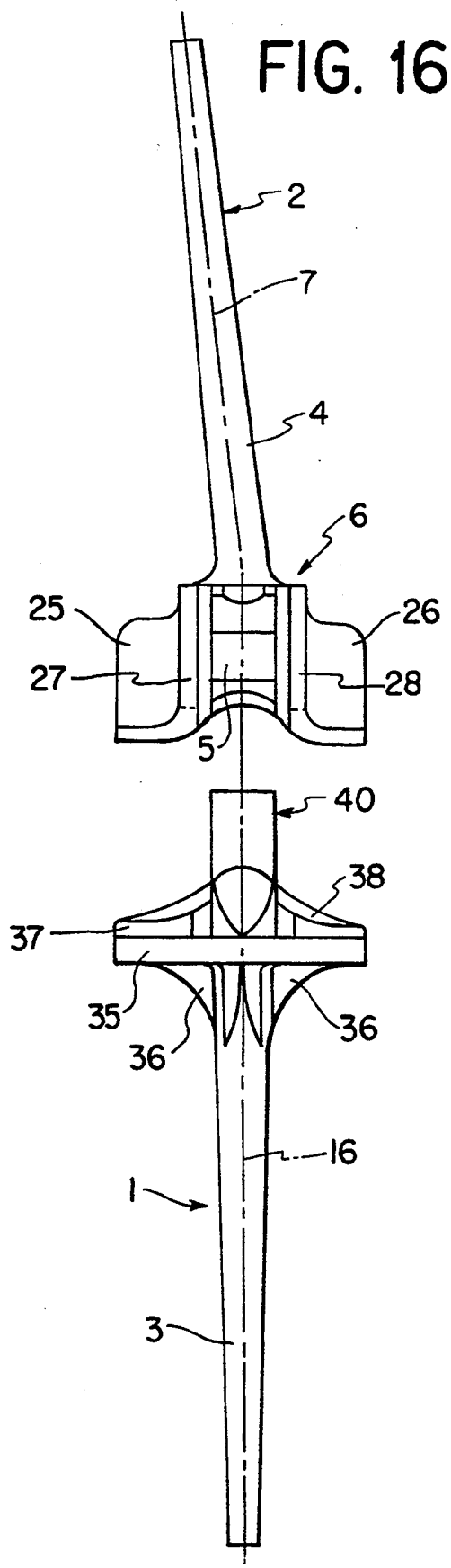
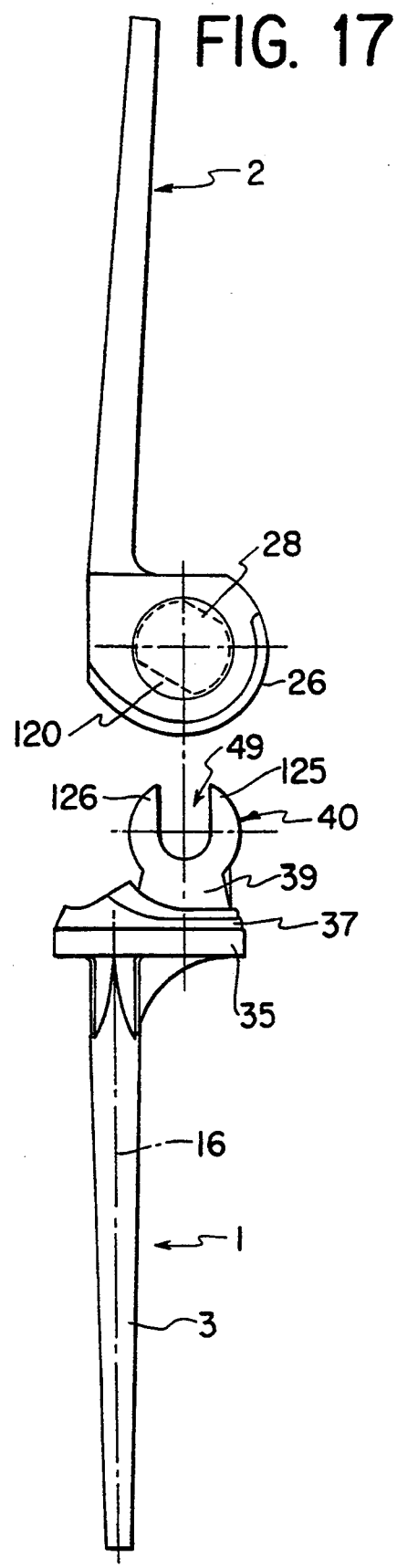

KNEE JOINT PROSTHESIS

This application is a continuation of U.S. application Ser. No. 07/800,327, filed Nov. 29, 1991, now abandoned.

BACKGROUND OF THE INVENTION

The invention relates to prostheses in general, and more particularly to improvements in knee joint prostheses. Still more particularly, the invention relates to improvements in knee joint prostheses of the type wherein a tibial component has a shank which is to be implanted into the tibia, a femoral component has a shank which is to be implanted into the femur, and the two components are coupled to each other by a hinge joint (hereinafter called hinge for short) defining a pivot axis which is disposed at a fixed distance from the two components. Such prostheses enable the femur to pivot relative to the tibia (and/or vice versa) in a predetermined plane (which is normal to the pivot axis) between a first position in which the two shanks make an oblique angle and a second position in which the two shanks extend from the pivot axis in substantially diametrically opposite directions.

Knee joint prostheses of the above outlined character are implanted when the tissue in the region of the knee joint to be replaced is no longer capable of properly connecting the femur with the tibia. Once the substance at the knee joint of a patient has been diagnosed as being incapable of properly connecting the tibia and the femur, it is equally impossible to replace the natural knee joint with an endoprosthesis of the type wherein the hinge which enables the tibia and the femur to pivot relative to each other is capable of permitting movements in the longitudinal direction of the tibia and/or femur. The stability of endoprosthesis of the just outlined character is achieved in that the two parts of the endoprosthesis are form-lockingly connected to each other. The damaged tissue at the knee joint is incapable of stabilizing an endoprosthesis to prevent undue material stresses of the system and/or luxations by permitting a shifting of the hinge. Moreover, such movements would cause considerable pain to the patient and would render a luxated endoprosthesis useless for its intended purpose.

The above outlined problems are much less acute when the natural knee joint is replaced with a fixed hinge type knee joint prosthesis because neither the tibial component nor the femoral component can move in the radial direction of the pivot axis which is defined by the hinge. Such complete form-locking engagement between the leaves of the hinge as well as between the leaves and the respective (femoral and tibial) components contributes significantly to the stability of the prosthesis, and the likelihood of damage to the material of the prosthesis is negligible or nil. The femur and the tibia can pivot relative to each other within preselected limits but are incapable of performing any other relative movements. It will be appreciated that a prosthesis wherein the pivot axis which is defined by the pintle of the hinge is disposed at a fixed distance from the femoral and tibial components is less versatile than certain other prostheses wherein the pivot axis can move longitudinally of the tibia and/or femur and/or vice versa. Therefore, the movements which such prosthesis permits are not identical with movements of a healthy knee joint but constitute a compromise between natural movements and those which are permissible or acceptable in view of the nature of damage or injury to the replaced natural knee joint. Thus, the tibia is not free to move from side to side but can merely turn about a single axis which is defined by the pintle of the hinge.

Heretofore known attempts to enhance the versatility of a knee joint prosthesis include the utilization of a hinge which permits the femur and the tibia to move relative to each other about a plurality of different axes. Such pronounced movability must be achieved without risking a loosening of the tibial and/or femoral component in the respective bone. In accordance with a presently known proposal, the artificial knee joint is to permit angular movements of the tibia and femur about a so-called compromise axis which is defined by a part attached to the femur. Extensive experiments with such prostheses indicate that a satisfactory orientation of the compromise pivot axis is yet to be found. If the axis of an existing prosthesis is not fixed, its orientation is far from resembling that which is defined by a natural knee joint and, in addition, a knee joint prosthesis with a non-fixed pivot axis is unreliable and does not permit the patient to perform movements which even remotely resemble those of a natural knee joint.

Another drawback of heretofore known knee joint prostheses is that they develop mechanical problems in the region of the hinge and/or at the loci of implantation of tibial and femoral components into the respective bones. In fact, the adverse mechanical influences are frequently so pronounced that it becomes necessary to remove the implanted prosthesis and to replace it with a different artificial knee joint. Implantation of a fresh knee joint prosthesis almost invariably necessitates extensive resection of bones which leads to substantial losses of bone material and causes complications in the course of subsequent operations.

Additional problems arise in connection with the implantation of knee joint prostheses. This holds especially true for proper positioning of threaded fasteners or other locating, retaining and/or positioning parts which must be anchored in a bone or which must pass through an accurately selected portion of a bone in order to properly engage complementary parts in the implanted prosthesis. Heretofore known proposals to accurately position material removing apparatus with reference to the bones to be drilled and/or similarly treated are far from satisfactory.

OBJECTS OF THE INVENTION

An object of the invention is to provide a novel and improved knee joint prosthesis which is simple, compact and inexpensive and, in addition, permits the tibia and the femur to perform movements which rather closely resemble the movements of such bones relative to a natural knee joint.

Another object of the invention is to provide a novel and improved hinge for use in the above outlined knee joint prosthesis.

A further object of the invention is to provide novel and improved leaves for use in the above outlined hinge.

An additional object of the invention is to provide an improved knee joint prosthesis of the type wherein the pivot axis which is defined by the pintle of the hinge is disposed at a fixed distance from the femur and from the tibia.

Still another object of the invention is to provide a novel and improved positioning for the hinge and its pivot axis relative to the femur and tibia.

A further object of the invention is to provide a novel and improved connection between a part of the hinge and the tibial component of the above outlined knee joint prosthesis.

Another object of the invention is to provide a novel and improved connection between a part of the hinge and the femoral component of the above outlined knee joint prosthesis.

An additional object of the invention is to provide a prosthesis which is less likely to become loose than heretofore known knee joint prostheses.

A further object of the invention is to provide novel and improved shanks for the femoral and tibial components of the above outlined knee joint prosthesis.

An additional object of the invention is to provide a novel and improved method of assembling and implanting the above outlined knee joint prosthesis.

Still another object of the invention is to provide a novel and improved apparatus for making holes in selected portions of bones preparatory to, during or subsequent to implantation of the femoral and/or tibial component.

An additional object of the invention is to provide an apparatus which can be utilized with particular advantage in connection with the implantation of the above outlined knee joint prosthesis.

A further object of the invention is to provide a versatile apparatus which can be rapidly and readily adjusted for the making of holes in selected portions of different bones.

Another object of the invention is to provide a simple, compact and inexpensive apparatus which can be utilized to properly locate and guide available drilling tools.

SUMMARY OF THE INVENTION

One feature of the present invention resides in the provision of a knee joint prosthesis which comprises a tibial component, a femoral component and a hinge which connects the two components for relative angular movement between first and second positions about a predetermined pivot axis in a predetermined pivoting plane extending substantially at right angles to the pivot axis. The tibial and femoral components respectively have second and third axes respectively located in substantially parallel second and third planes which (in the first positions of the two components) are substantially parallel to a fourth plane including the pivot axis. The third and fourth planes are spaced apart from each other a first distance, and the second and fourth planes are spaced apart a second distance less than the first distance in the first positions of the two components. The hinge includes first and second leaves which are respectively movable with the tibial and femoral components, and the two components are arranged to contact each other at a fifth plane which is spaced apart a third distance from a sixth plane including the pivot axis and being normal to the fourth plane.

The fifth plane is substantially tangential to a line which is disposed in a seventh plane of contact between the two components, and the aforementioned line is normal to the pivoting plane when the two components are caused to assume their second positions, the second and third planes define an oblique angle which has an apex. The femoral component has a rear portion (as seen subsequent to implantation of the prosthesis) which is located at the apex in the second positions of the two components.

The tibial and femoral components respectively comprise first and second shanks, and the third plane crosses the first shank in the first positions of the two components.

The second and third planes are preferably spaced apart from each other a fourth distance which is preferably between approximately 0.5 and 4 mm, most preferably between 1.5 and 2.5 mm, in the first positions of the two components. The first distance is preferably between 16 and 21 mm, most preferably approximately 16 mm. The third distance is preferably between approximately 20 and 24 mm, most preferably approximately 21 mm.

At least one of the two shanks is preferably elongated and has a predetermined length and a maximum transverse dimension which is or can be a small or minute fraction of the predetermined length. Furthermore, at least one of the shanks can taper in a direction away from the hinge and away from the other shank. Still further, at least one of the shanks is preferably devoid of undercut portions. That end portion of at least one shank which is remote from the hinge can be provided with means for centering such shank in a bone of a patient. The centering means is or can be substantially star shaped, and at least a portion of the centering means can consist of a plastic material.

At least one of the shanks can have a polygonal cross-sectional outline; for example, the at least one shank can have a square or rectangular cross-sectional outline with rounded edges between neighboring external surfaces.

One of the components (preferably the femoral component) has an end which is adjacent the hinge, and the respective leaf of the hinge preferably comprises a housing having two spaced apart walls which extend from the shank toward the component (preferably the tibial component) which is movable with the other leaf. The hinge can further comprise an annular bearing element at each of the two walls, and a pintle which defines the predetermined pivot axis and extends into the bearing elements. One of the bearing elements can be provided with a blind hole for one end portion of the pintle, and the other bearing element can be provided with a through hole which receives and affords access to the other end portion of the pintle. The two holes have a common axis when the bearing elements are properly installed in the housing. At least one of these bearing elements can consist of a plastic material, such as polyethylene. The walls of the housing can be provided with complementary sockets for the bearing elements.

The housing is provided with a chamber, and the walls have confronting parallel surfaces which are adjacent the chamber. The aforementioned sockets can be provided in the surfaces of the two walls, and the bearing elements have surfaces which are preferably flush with the surfaces of the respective walls when the bearing elements are properly installed in their sockets. The bearing elements can be provided with rims which are received in the respective sockets and are preferably adjacent the surfaces of the respective walls.

The outer sides of the walls of the housing (such outer sides face away from the chamber) are preferably provided with extensions or wings having arcuate surfaces facing the tibial component. The latter has surfaces which contact or can contact the extensions of the walls which form part of the housing. Each extension can have a pronounced width in the direction of the pivot axis, and the arcuate surfaces of the extensions can be closely adjacent a bearing surface of the tibial component. The width of the housing (as seen in the direction of the pivot axis) can be twice the width of an extension or wing.

Each arcuate surface can constitute a convex surface, and the extensions have edge faces which are remote from the respective walls. Each convex surface extends from the respective wall to the edge face of the respective extension, and the tibial component has end faces which are congruent with the edge faces of the extensions.

The walls of the housing preferably extend concentrically with the pivot axis along arcs of approximately 180°.

The arcuate surfaces of the extensions are located at that side of the femoral component which confronts the tibial component. A rear portion of the femoral component is adjacent the rear end portions of the extensions, and the aforementioned side of the femoral component preferably crosses the sixth plane at the rear portion of the femoral component. The sixth plane is a horizontal plane in implanted condition of the two components, and the rear end portions of the two extensions are then located at a level slightly above the horizontal plane.

Each extension has a front end portion and a rear end portion, and each extension extends about the pivot axis along the aforementioned arc from the respective rear end portion to the respective front end portion at a front face of the femoral component. Such front face is located opposite the rear portion of the femoral component. The front end portions of the extensions are spaced apart from the sixth plane a fourth distance in a direction toward the tibial component, and the rear end portions of the extensions are spaced apart from the sixth plane a fifth distance in a direction away from the tibial component. The fifth distance can at least approximate the fourth distance, and the arc along which the extensions extend about the pivot axis can have sections of different curvature. Such sections can include sections of less pronounced curvature at the end portions of the extensions and at least one section of more pronounced curvature between the end portions of the extensions.

The leaf which is rigid with the femoral component preferably comprises an arcuate bridge which connects the front end portions of the two extensions. The bridge is located at the front face of the housing, and the tibial component can be provided with a protuberance which is adjacent and substantially complementary to the bridge.

The leaf which is provided on the tibial component preferably comprises a flange which at least substantially fills the chamber of the housing in assembled condition of the hinge. The flange can be provided with an opening for the median portion of the pintle. The end portions of the pintle are received in the housing, preferably in a manner as described hereinbefore. The flange has two lateral surfaces which are at least substantially parallel to each other and are disposed at opposite sides of the pivoting plane. The internal surfaces of the housing are adjacent the lateral surfaces of the flange when the latter is received in the chamber, and the two lateral surfaces are then equidistant from the pivoting plane. The chamber can have a substantially rectangular cross-sectional outline in a plane which is normal to the pivoting plane, and the internal surfaces of the housing flank the chamber which latter is further bounded by a surface provided on the housing and extending in substantial parallelism with the second plane in the first positions of the two components. The chamber is preferably open opposite the last named surface.

The leaf which includes the flange can further comprise a preferably plate-like base which is substantially normal to the second axis, and the flange is or can be disposed substantially centrally of the base. The flange can but need not comprise an eyelet. Such eyelet has a circular opening for the median portion of the pintle, and a convex external surface with a center of curvature on the pivot axis. Still further, the leaf which includes the flange and the base can also comprise a bearing shell or trough which is provided on the base. The flange extends through the shell in a direction from the base toward the femoral component. The shell can be U-shaped and then comprises two legs which flank the flange and a web which connects the two legs to each other at the front side of the base. The flange can be adjacent the rear side of the base. The shell includes a bearing surface which confronts the femoral component and is engageable by the extensions of the housing. The bearing surface extends from the front side toward the rear side of the base. The front end portions of the extensions are engageable with the front portion of the bearing surface, and the bearing surface further includes a substantially plane rear portion. The front portion extends beyond the rear portion of the bearing surface in a direction toward the femoral component. The rear portion of the bearing surface is contacted by the one and/or the other extension in the second positions of the two components. The sliding surfaces of the two extensions serve to contact the bearing surface of the shell. The arrangement is such that at least one of the extensions engages the bearing surface in response to the application of a force which urges the two components toward each other.

The bearing surface of the shell can further include a substantially concave intermediate portion which is located between the front and rear portions and preferably includes a steep front part adjacent the front portion of the bearing surface. Such steep part can constitute approximately one-third of the intermediate portion of the bearing surface. The latter can be further provided with recessed guide portions for the extensions of the housing.

The shell can be made of a plastic material, e.g., polyethylene.

The hinge can further comprise means for non-rotatably securing the pintle to the flange. Such securing means can include a grub screw or another threaded fastener. One end face of the pintle can be provided with an axially extending recess for the working end of a tool which facilitates insertion of the pintle into the housing and into the flange. The pintle can consist, at least in part, of a metallic material.

The bearing elements for the end portions of the pintle can be made of a plastic material, and the pintle is or can be mounted in such a way that its end portions are rotatable in the respective bearing elements. The extensions of the housing can consist of a hard metal.

At least one of the two shanks can be made of an elastically deformable material.

The aforementioned eyelet-shaped flange of the leaf on the tibial component can be replaced with a substantially U-shaped flange having a slot which has an open end facing the femoral component. Such U-shaped flange can be received in the aforementioned housing, and the median portion of the properly installed pintle is located in the slot of the flange in the housing. The arrangement may be such that the pintle is insertable into the slot only in the second positions of the two components. The U-shaped flange can be further provided with a bolt which extends across the open end of its slot to confine the median portion of the pintle in the slot. The bolt can be form-lockingly connected with at least one leg of the U-shaped flange; such bolt can be held in an operative position by a grub screw or another threaded fastener.

Another feature of the present invention resides in the provision of an apparatus for making a hole in a selected portion of a bone. The improved apparatus comprises a locating member which is movable to a position of alignment with the selected portion of the bone, a tubular guide member which is aligned with and is spaced apart from the locating member so that the selected portion of the bone can be positioned between the two members and a drilling tool, which is introduced into the guide member, can drill a hole into the thus positioned selected portion of the bone in a direction toward the locating member, and means for connecting the locating and guide members to each other. The drilling tool can constitute a rotary cup-shaped drill which can receive a plug constituting the removed selected portion of the bone.

The connecting means preferably comprises at least one distancing element, particularly a substantially U-shaped distancing element which includes a first leg affixed to the locating member and a second leg affixed to the guide member. The apparatus can further comprise an elongated carrier (hereinafter called handle) in the form of a bar or rod which is connected with a selected section of the distancing element. For example, if the distancing element is substantially U-shaped and includes a first section in the form of the aforementioned first leg, a second section in the form of the aforementioned second leg, and a third section in the form of a web which connects the first and second legs to each other, one end portion of the handle can be made rigid with an intermediate part of the third section and the other end portion of the handle can carry a handgrip portion (e.g., a wheel or the like) to facilitate manipulation of the handle and of the parts which are carried by it. The handgrip portion can extend transversely of the longitudinally extending axis of the handle.

The apparatus can further comprise a support which is mounted on and is movable longitudinally of the handle, and a hammer or striker which is mounted on and is movable longitudinally of the handle against the support. The support is disposed between the distancing element and the hammer, i.e., the hammer is installed between the support and the handgrip portion. The support can include a follower which is movable along and preferably at least partially surrounds the handle. Such support can further comprise means (e.g., in the form of a screw or another threaded fastener) for releasably securing the follower (and hence the support) to a selected part of the handle.

The support can further comprise an anvil which is movable along the handle, after the follower is released for movement relative to the handle, to and from a position of register with the locating member in such a way that the locating member is located between the anvil and the guide member, This apparatus can be used for making a hole in a bone into which is already implanted a shank carrying a housing with a chamber bounded by two surfaces which are spaced apart a predetermined distance from each other and one of which has a hole aligned with the selected portion of the bone. The anvil and the locating member (with its leg) are insertable into the chamber, and the anvil and the leg have a combined thickness which at least closely approximates the aforementioned distance between the two surfaces in the housing. The locating and guide members have a common axis, and the housing can contain an annular bearing element which is coaxial with the locating and guide members when the selected portion of the bone is located between such members. Alternatively, the apparatus can be furnished with one or two temporary annular bearing elements which are receivable in sockets provided in the aforementioned surfaces of the housing and are installed in such sockets during the making of a hole in the selected portion of the bone.

The support can further comprise an arm and/or other suitable means for connecting the follower with the anvil. The hammer can be used as a means for gently tapping on the anvil in order to drive the latter into the chamber between the locating member and one of the surfaces in the housing preparatory to drilling of a hole into the selected portion of the bone.

The novel features which are considered as characteristic of the invention are set forth in particular in the appended claims. The improved prosthesis itself, however, both as to its construction and the mode of implanting the same, together with additional features and advantages thereof, will be best understood upon perusal of the following detailed description of certain presently preferred specific embodiments with reference to the accompanying drawing.

BRIEF DESCRIPTION OF THE DRAWING

FIG. 1 is a partly sectional exploded view of a knee joint prosthesis which embodies one form of the invention, the pintle of the hinge being omitted and the section being taken along the line I—I in FIG. 2 as seen in the direction of arrows;

FIG. 2 is a side elevational view as seen from the left-hand side of FIG. 1;

FIG. 3 is an elevational view of the pintle and an axial sectional view of two annular bearing elements for the end portions of the pintle;

FIG. 4 is an enlarged fragmentary elevational view of the free end portion of the shank of the femoral component of the prosthesis;

FIG. 5 is a schematic side elevational view of the assembled prosthesis, with the tibial and femoral components shown in their first angular positions;

FIG. 6 shows the structure of FIG. 5 but with the two components in the second angular positions;

FIG. 7 is a smaller-scale schematic elevational view of the femoral component, of two bearing elements of the type shown in FIG. 3, and of two temporary annular bearing elements which can be used during the making of a hole in a selected portion of the femur;

FIG. 16 is an exploded view of a modified knee joint prosthesis;

FIG. 17 is a side elevational view as seen from the left-hand side of FIG. 16;

DESCRIPTION OF PREFERRED EMBODIMENTS

Figure 8:
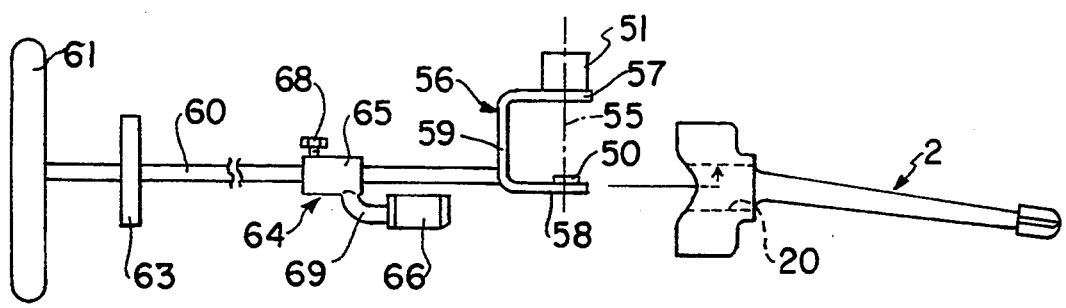
FIG. 8 is a schematic elevational view of an apparatus which can be used to drill a hole in the femur and a schematic elevational view of the femoral component, the locating member of the apparatus being in the process of advancing toward the chamber in the housing of the hinge leaf on the femoral component.
Figure 9:
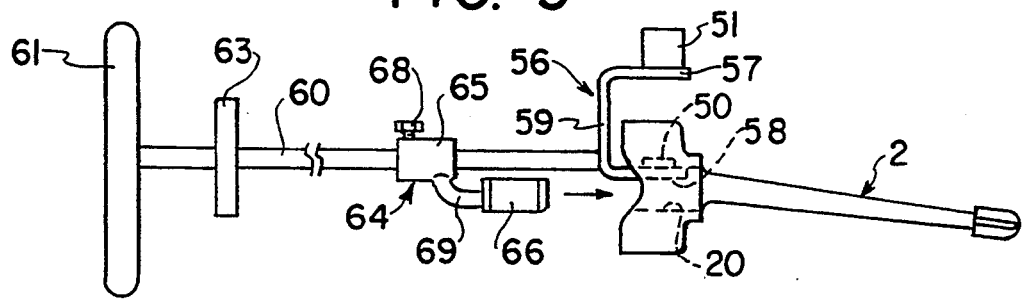
FIG. 9 shows the structure of FIG. 8 but with the apparatus in an operative position ready to guide a drilling tool into a selected portion of the femur.
Figure 10:
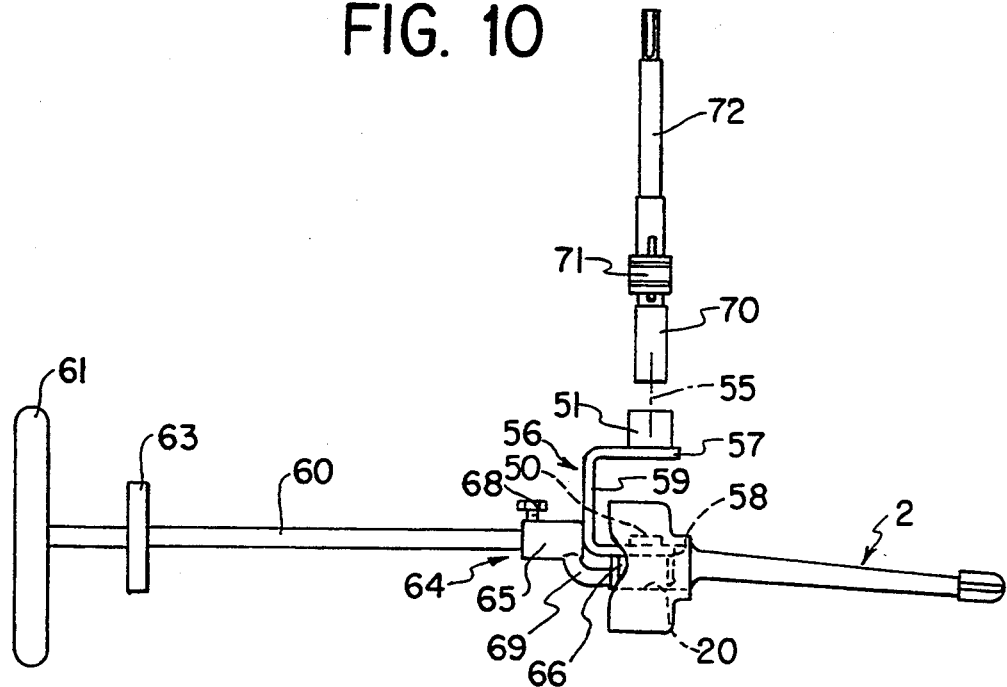
FIG. 10 shows the structure of FIG. 9 and a drilling tool which is about to enter the tubular guide member 5 of the apparatus.

Referring first to FIGS. 1 to 6 there is shown a knee joint prosthesis which includes, essentially, a tibial component 1 with an elongated shank 3 having a longitudinal axis 16, a femoral component 2 having an elongated shank 4 with a longitudinal axis 7, and a hinge which serves to articulately connect the components 1, 2 to each other for angular movement about a predetermined pivot axis 12 defined by a pintle or shaft 5. In addition to the pintle 5, the hinge comprises a leaf constituted primarily by a housing 6 at that end of the component 2 which is adjacent the component 1, and a leaf including a flange 33 in the form of an eyelet rigid with the component 1 and having an axial bore or hole or opening 34 for a median portion of the pintle 5. The leaf which is provided on the tibial component 1 further comprises a substantially plate-like base 35 which is rigid or integral or of one piece with the adjacent end portion of the component 1, and a bearing shell or trough 37 which overlies the base 35 at that side which confronts the femoral component 2. The flange 33 is located substantially centrally of the base 35 and extends toward the femoral component 2 through a slot between the adjacent legs 101, 102 of the substantially U-shaped shell 37.

The shank 3 is implantable into a complementary bore or hole in the tibia of a patient, and the shank 4 is implantable in the femur. FIG. 5 shows the mutual angular positions of the shanks 3, 4 when a (second) plane 97 which includes the axis 16 of the shank 3 is at least substantially parallel to a (third) plane 123 which includes the axis 7 of the shank 4. These planes are normal to a horizontal (sixth) plane 79 and parallel to a vertical (fourth) plane 78. The planes 78, 79 cross each other along the normally horizontal pivot axis 12 which is defined by the pintle 5 when the latter is properly installed in the walls 8, 9 of the housing 6 and in the opening 34 of the flange 33. At such time, the flange 33 extends into and at least substantially fills a chamber 20 of the housing 6. The mounting of the pintle 5 is preferably such that its median portion is non-rotatably secured to the flange 33 and that its end portions are rotatable in the walls 8, 9 of the housing 6.

The reference character 96 denotes in FIG. 2 a predetermined (first or pivoting) plane in which the shank 4 is movable about the axis 12 of the pintle 5 when the femur is caused to pivot relative to the tibia, e.g., between the angular positions of FIGS. 5 and 6. The pivoting plane 96 is normal or substantially normal to the axis 12 and hence to the fourth and sixth planes 78, 79, The axes 7, 16 and the respective (third and second) planes 123, 97 make an oblique angle 111 (FIG. 6) when the shank 4 assumes the inclined or second position 110 shown in FIG. 6. A rear portion 112 of the femoral component 2 is located at the apex of the angle 111 when the component 2 assumes the inclined (second) angular position 110 of FIG. 6, At such time, the rear portion 112 of the femoral component 2 is adjacent but still spaced apart from the rear portion 113 of the tibial component 1. The illustrated oblique angle 111 between the axes 7, 16 exceeds 90°.

The sidewalls 8, 9 of the housing 6 have internal surfaces 98, 99 (FIGS. 1 and 3) which are provided with sockets 10, 11 for the respective annular bearing elements or bearings 27, 28. The internal surfaces 98, 99 are parallel to each other and coincide with the inner surfaces of the properly installed bearing elements 27, 28. These bearing elements have circular rims 23, 24, respectively, which are received in the corresponding sockets 10, 11, i.e., in the respective walls 8, 9 of the housing 6. The common axis of the properly inserted bearing elements 27, 28 coincides with the axis 12 of the properly installed pintle 5.

The (first) distance 13 of the third plane 123 (including the axis 7 of the shank 4) from the vertical fourth plane 78 in the first angular positions of the components 1, 2 relative to each other (see FIG. 5) is normally between approximately 16 and 22 mm, preferably at least close to 16 mm. The distance 13 slightly exceeds a (second) distance 121 of the fourth plane 78 from the second plane 97 (including the axis 16 of the shank 3). A third distance of the horizontal sixth plane 79 from a horizontal (fifth) plane 114 of sliding contact between the components 1, 2 in their second positions (see FIG. 6) is shown at 15. The horizontal plane 114 is tangential to a line 115 which, in turn, is normal to the pivoting plane 96 and is located in a (seventh) plane 117. The plane 117 is located opposite the arcuate (convex) surfaces 14 at the adjacent sides of two substantially wing-shaped extensions 25, 26 which project from the outer sides of the respective walls 8, 9 and are parts of the housing 6 as well as of the femoral component 2. The surfaces 14 contact a bearing surface 38 Of the shell 37, at least when the tibial component 1 is pivoted relative to the femoral component 2 about the axis 12 of the pintle 5 or vice versa.

The axis 7 of the shank 4 is inclined relative to the axis 16 of the shank 3 (see FIG. 1). The inclination of the axis 7 of the shank 4 relative to the axis 16 of the shank 3 corresponds to the median or average value of a so-called valgus angle.

The annular bearing elements 27, 28 can be a close fit in the sockets 10, 11 of the respective walls 8, 9. The bearing elements 27, 28 further include surfaces 21, 22 which are adjacent to the respective rims 23, 24 and to the chamber 20 between the walls 8, 9 of the housing 6, and surfaces 18, 19 which abut the respective walls 8, 9. It can be said that the internal surfaces 98, 99 of the walls 8, 9 are defined by the bearing elements 27, 28 which, upon insertion into their sockets 10, 11, can be considered as constituting component parts of the respective walls. The bearing elements 27, 28 can be made of a suitable plastic material, preferably polyethylene, and are in sliding contact with the respective lateral surfaces 93, 94 of the flange 33 when the latter is received in and at least partially fills the chamber 20 of the housing 6. In other words, the surfaces 98, 99 respectively contact the surfaces 93, 94 when the hinge is properly assembled, i.e., when the housing 6 and the flange 33 are articulately connected to each other by the pintle 5 which then extends into a blind hole 29 of the bearing element 27 and into an axially aligned through hole 31 of the bearing element 28. The deepmost portion of the blind hole 29 is adjacent a relatively thin bottom wall 30 which forms part of the bearing element 27 (see particularly FIG. 3) and serves as an abutment for the adjacent end face of the properly installed pintle 5. The diameters 32 of the holes 29, 31 match or only negligibly exceed the diameter of the pintle 5. This ensures that the pintle 5 is held against any, or against appreciable, radial movements relative to the housing 6 and relative to the bearing elements 27, 28 in the respective walls 8, 9 of the housing. At the same time, the left-hand end face of the pintle 5 (as seen in FIG. 3) abuts the bottom wall 30, and the pintle is held against axial and angular movement relative to the flange 33 by a removable fastener 46 in the form of a grub screw having external threads adapted to mate with internal threads 45 of a tapped radial bore 44 in the periphery of the median portion of the pintle.

The outer sides of the walls 8, 9 (namely the sides which face away from the respective surfaces 98, 99 and hence away from the chamber 20 of the housing 6) are provided with the aforementioned outwardly projecting extensions 25, 26 in the form of wings which are relatively wide as measured in the direction of the pivot axis 12. The extensions 25, 26 have an arcuate shape and extend circumferentially of the axis 12 of the pintle 5 along an arc 87 (FIG. 2). The front end portions of the extensions 25, 26 are indicated at 88, and the rear end portions of these extensions are indicated at 83. The extensions 25, 26 are located at the underside of the femoral component 2, i.e., at that side (82) which confronts the adjacent end of the tibial component 1. As can be seen in FIG. 1, the underside 82 has a concave inner or central portion which merges into convex intermediate portions which, in turn, merge into substantially flat end portions. The surfaces 14 of the extensions 25, 26 form part of the underside 82 of the femoral component 20 Since the extensions have a pronounced width in the axial direction of the pintle 5, their surfaces 14 are relatively wide and can come into large-area contact with the adjacent portions of the tibial component 1, and more particularly with the afore-mentioned bearing surface 38 at the upper side of the shell 37 on the base 35 which latter is affixed to or is made of one piece with the tibial component 1. The bearing surface 38 is located at the (seventh) plane 117 and has an arcuate shape. The curvature of those portions or sections of the bearing surface 38 which are in, or can come into, contact with the extensions 25, 26 preferably conforms (at least substantially) to the curvature of the respective surfaces 14.

The width of each of the two extensions 25, 26 (as measured in the direction of the pivot axis 12) can equal or approximate half the width of the housing 6. The surfaces 14 of the extensions 25, 26 are slightly convex, and the convexity decreases gradually in directions toward the respective lateral end faces or edge faces 80, 81 of the respective extensions. The edge faces 80, 81 are at least substantially parallel to and remote from the surfaces 98, 99 of the bearing elements 27, 28. Furthermore, the edge faces 80, 81 are at least substantially congruent with the adjacent end faces or edge faces 84, 85 of the base 35 for the flange 33 and shell 37. The upper side of the base 35 is located in or close to the aforementioned seventh plane 117.

As can be seen in connection with the extension 25 of FIG. 2, the two extensions 25, 26 extend along arcs 87 of approximately 180°. The centers of curvature of these extensions are located on or at least close to the axis 12 of the pintle 5 in assembled condition of the prosthesis. The rear end portions 83 of the extensions 25, 26 are adjacent the rear portion 112 of the femoral component 2. A line 86 denotes in FIG. 2 the location of intersection of the sixth plane 79 with the underside 82 of the femoral component 2. The rear end portions 83 of the extensions 25, 26 are located at such intersection and are disposed slightly above the plane 79 in the extended position of the prosthesis, i.e., in the position corresponding to that shown in FIG. 5. The rear end portions 83 are adjacent the plane 117 when the femoral component 2 is pivoted to the inclined position 110 of FIG. 6.

The front end portions 88 of the extensions 25, 26 are adjacent the front face 89 of the housing 6. These front end portions 88 are located at a level below the horizontal plane 79 (in contrast to the rear end portions 83) when the femoral component 2 is pivoted to the extended or first position of FIG. 5, At such time, the distance between the front end portions 88 and the plane 79 is or can be the same as the distance of such plane from the rear end portions 83 except, of course, that the front and rear end portions of the extensions 25, 26 are then located at opposite sides of the plane 79.

The curvature of the extensions 25, 26 along the arc 87 varies from section to section of the arc. Thus, the curvature of sections is less pronounced (the radii of curvature are larger) at the front and rear end portions 83, 88 but is more pronounced in the median or central section 90, The front end portions 88 of the extensions 25, 26 are connected to each other by a relatively short arched bridge 91 (FIG. 1) which has a concave underside confronting the tibial component 1. The bridge 91 is located at a front surface 92 of the housing 6.

The distance 95 of lateral surfaces 93, 94 of the flange 33 from each other at least approximates the distance of the surfaces 98, 99 from one another, and the surfaces 93, 94 are disposed at opposite sides of and at the same distances from the pivoting plane 96.

The chamber 20 of the housing 6 has a substantially rectangular cross-sectional outline in a plane which is normal to the pivoting plane 96. This chamber is closed in a direction toward the front end portions 88 of the extensions 25, 26 (by the front surface 92) but is open in a direction toward the rear portions 83 of the extensions.

The flange 33 resembles or constitutes an eyelet with the aforementioned centrally located circular opening for the median portion of the pintle 5, and with a convex external surface 100 having its center of curvature on the axis 12. The reference characters 36 denote in FIG. 1 reinforcing ribs or webs which extend between the underside of the base 35 and the adjacent portions of the shank 3.

The bearing shell 37 is U-shaped and includes the aforementioned legs 101, 102 which are adjacent the respective lateral surfaces 93, 94 of the flange 33 and a web or yoke 104 which extends between the legs 101,102 adjacent the front side 103 of the base 35. The front side 103 is adjacent the front surface or side 89 of the housing 6. The flange 33 extends from the base 35, through a slot 105 between the legs 101, 102 of the shell 37 and toward the femoral component 2, namely into the chamber 20 of the housing 6. The locus where the flange 33 extends through the slot 105 of the shell 37 is adjacent the rear side 106 of the base 35.

As mentioned above, that side of the shell 37 which confronts the femoral component 2 constitutes a bearing surface 38 for the surfaces 14 of the extensions 25, 26 on the housing 6. The bearing surface 38 has a substantially plane rear portion or section 108 adjacent the rear side 106 of the base 35, and a front section or portion 107 which slopes outwardly from the rear section 108 in a direction toward the femoral component 2. The plane or nearly plane rear section 108 of the bearing surface 38 can actually merge into the upper side (117) of the base 35 at the rear section 106 of the base. The front section 107 is adjacent the web or yoke 104 and confronts the front end portions 88 of the extensions 25, 26, The rear section 108 is located in the plane 117.

When the stress upon the femoral component 2 is uniformly distributed so that it can be taken up by the extension 25 as well as by the extension 26, the surfaces 14 at the undersides of the two extensions are in sliding contact with the bearing surface 38 of the shell 37. If the stresses are not uniform, the bearing surface 38 is engaged by the surface 14 of the extension 25 or 26. Such design ensures that the flange 33 is not deformed at the locus (39) of its connection with the base 35 when the distribution of stresses among the extensions 25, 26 is not uniform. It is to be borne in mind that the flange 33 extends into and at least substantially fills the chamber 20 of the housing 6, i.e., the surfaces 93, 94 are closely adjacent and normally contact the surfaces 98, 99 of the respective bearing elements 27, 28 when the hinge including the pintle 5, the housing 6 and the flange 33 is properly assembled.

The bearing surface 38 is further provided with a concave intermediate portion or section 116 which is disposed between the front section 107 and the rear section 108. That part (for example, approximately or exactly one-third) of the intermediate section 116 which is adjacent the front section 107 has a slope steeper than that of the part adjacent the rear section 108. Still further, the bearing surface 38 is provided with notches or recesses or depressions for the surfaces 14. These notches or recesses extend transversely of the longitudinal direction of the shell 37 and are bounded by surfaces which are at least substantially complementary to the respective surfaces 14. This contributes to stabilization of the prosthesis while the components 1, 2 are caused to pivot relative to each other; at such time, the surfaces 14 roll along the surfaces in the respective recesses or grooves of the bearing surface 38. Such pivoting takes place while the front portion 103 of the base 35 form-lockingly guides the underside 82 of the housing 6.

The bearing shell 37 can be made of a plastic material, such as polyethylene. This ensures proper sliding and-/or rolling contact between the bearing surface 38 and the surfaces 14 of the extensions 25, 26. Such proper sliding and/or rolling contact takes place irrespective of the magnitude of stress upon the components 1, 2 in directions to urge the extensions 25, 26 toward the surface 38 of the shell 37.

The grub screw 46 of FIG. 3 can be introduced into the tapped bore or hole 44 in the median portion of the pintle 5 by passing through a radially extending opening or hole 41 in the external surface 100 of the flange or eyelet 33. When the screw 46 extends into the tapped bore 44 as well as into the opening 41, the pintle 5 is held against rotation relative to the flange 33. The outer end of the opening 41 is then filled with suitable bone cement which sets and thus prevents unintentional turning of the screw 46 when the implanted prosthesis is in use. Thus, the outer end of the properly installed and secured screw 46 cannot project beyond the surface 100 of the flange 33 and cannot damage the housing 6 subsequent to completion of the implanting step. Moreover, the pintle 5 remains non-rotatably connected to the flange 33, i.e., to the tibial component 1. When properly installed in the opening 34 of the flange 33, the pintle 5 causes its end portion 118 (FIG. 3) to project into the blind hole 29 of the bearing element 27, and the other end portion 119 of the pintle then extends into the through hole 31 of the bearing element 28.

Figure 12:
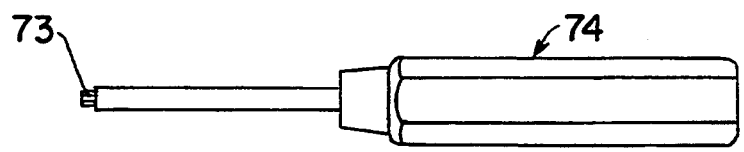
FIG. 12 is an elevational view of a tool which can be used to facilitate installation of the pintle.

FIG. 3 further shows that the right-hand end face (at the end portion 119) of the pintle 5 is formed with internal threads 43 in a tapped axially extending blind bore or recess 42 which can receive the externally threaded working end 73 of a suitable inserting tool or implement 74 (FIG. 12) serving to facilitate installation of the pintle in the housing 6 and in the flange 33. Once the screw 46 is driven home, i.e., once the pintle 5 is non-rotatably secured to the flange 33, the tool 74 is rotated in a direction to disengage the working end 73 from the internal thread 43 and to permit withdrawal of the working end 73 through the hole or bore 31 in the bearing element 28.

FIG. 4 shows that at least one of the shanks 3, 4 can be provided with a centering member 47 which is remote from the hinge and is inserted into the bore of the respective bone. In FIG. 4, the centering member 47 resembles a star with four prongs 48 and is located at that end of the shank 4 which is remote from the housing 6. A similar or a differently designed centering member can be provided at the free end of the shank 3. The centering member or members constitute desirable but optional features of the improved prosthesis, i.e., at least one of the components 1, 2 can be furnished without any centering means for the free end portion of its shank. If provided, the centering member is preferably mounted or formed in such a way that its axis coincides with the longitudinal axis (16 or 7) of the respective shank (3 or 4). The prongs or wings 48 stabilize the centering member 47 subsequent to implantation into a bone, and such wings center the respective shank in the course of the implanting step.

The (fourth) distance 122 between the second and third planes 97,123 (in the first angular positions of the components 1, 2 as shown in FIG. 5) is preferably between approximately 0.5 and 4 mm, most preferably between 1.5 and 2.5 mm.

The bearing elements 27, 28 and the bearing shell 37 can be made of a plastic material which can stand pronounced and long-lasting stresses. A presently preferred plastic material is polyethylene. The pintle 5 is preferably made of a suitable metallic material. However, it is equally within the purview of the invention to employ a pintle which comprises a metallic core in an envelope of polyethylene or another suitable plastic material. The bearing elements 27, 28 are then made of a metallic material. The wing-like extensions 25, 26 of the housing 6 are preferably made of a hard metallic material, and their surfaces 14 are preferably polished or otherwise treated to a high degree of finish.

As mentioned above, the distance 13 is preferably between approximately 16 and 21 mm. It has been found that a distance 13 of approximately 16 mm is particularly suited for a number of purposes. As also mentioned above, the distance 15 is preferably between approximately 20 and 24 mm. A distance 15 which is close to or exactly 22 mm has been found to be universally acceptable in a number of prostheses of the above outlined character.

The shanks 3 and 4 of the components 1 and 2 can be made of a metallic material. It is preferred to select the sizes of these shanks (or of at least one of these shanks) in such a way that the maximum transverse dimension of the shank 3 and/or 4 is but a small or minute fraction of the length of the respective shank. In other words, the length of the shank 3 and/or 4 in the direction of its axis 16 or 7 can be many times the maximum dimension as measured transversely of the respective axis. At least one of the shanks 3, 4 preferably tapers in a direction from the hinge toward the respective free end. Moreover, at least one of these shanks is preferably devoid of any undercuts (e.g., shoulders facing in a direction toward the hinge) because the undercut(s) would complicate the implanting step. This is particularly important if one takes into consideration that a knee joint prosthesis is expected to require replacement after a certain interval of use. Still further, at least one of the shanks can be made of a material which is at least slightly resilient so that the shank can flex with the respective bone (i.e., with the femur or with the tibia) to thus reduce the likelihood of loosening of the shanks in the respective bones.

It is presently preferred to configurate at least one of the shanks 3, 4 in such a way that the shank has a rectangular, particularly square, cross-sectional outline with at least partially rounded edges between neighboring external surfaces. Such configuration has been found to be particularly advantageous for a number of reasons; for example, because a shank having a substantially square cross-sectional outline can withstand pronounced bending and/or other stresses. Moreover, a shank having a polygonal cross-sectional outline is less likely to become loose in the respective bone in response to attempted turning of the femur relative to the tibia and/or vice versa. Still further, such design of the shank 3 and/or 4 reduces the likelihood of development of fatigue. The dimensions of the shank 3 may but need not be the same as those of the shank 4. Moreover, the material of the shank 3 may but need not be the same as that of the shank 4.

The prosthesis of FIGS. 1-6 satisfies several important requirements which must be met in order to ensure that the movements of the knee joint of a person having the improved prosthesis implanted in her or his femur and tibia will resemble the movements of a natural knee joint. The following are some of numerous advantages of the improved prosthesis:

(1) The second plane 97 is slightly offset relative to the third plane 123 (note the aforediscussed distance 122) when the components 1 and 2 assume the first or extended positions of FIG. 5. At such time, the plane 123 intersects the shank 3 of the tibial component 1. Otherwise stated, the axis 16 of the shank 3 of the tibial component 1 is nearer to the rear portions 113, 112 of the components 1, 2 than the axis 7 of the shank 4 of the femoral component 2. Such selection of the locations of axes 16, 7 ensures that the transmission of forces from the femoral component 2 into the tibial component 1 or vice versa presents no problems when the improved prosthesis is in actual use. In other words, such positioning of the axes 16, 7 relative to each other ensures an optimal positioning and guidance of the femur relative to the tibia and/or vice versa.

(2) The pivot axis 12 of the properly installed pintle 5 is nearer to the rear portions 113, 112 of the components 1, 2 than to the front portions (see FIGS. 2, 5 and 6), This enables the person in charge of designing the prosthesis for a particular patient to select appropriate horizontal distances between various planes, surfaces and parts; such distances vary from patient to patient. Proper selection of the just mentioned distances is important for optimal transfer of stresses from the femur into the tibia and in the opposite direction. This, in turn, reduces the likelihood of excessive stressing of the femur and/or tibia when the prosthesis is in use. Moreover, the aforementioned selection of the locus of the pivot axis 12 does not interfere with the establishment of circumstances which are necessary for proper confinement of soft tissue in the bight between the two parts of a patient's leg which are articulately connected to each other by the improved prosthesis. Thus, the shanks 3, 4 and/or the rear portions 113, 112 of the components 1, 2 are highly unlikely to pinch and/or otherwise adversely affect the tissue within the arc 111 which is shown in FIG. 6. Moreover, the components 1, 2 can be implanted with a minimum of resection, and the implanted prosthesis ensures proper anatomical positioning of the femur and tibia relative to each other. Still further, and since the planes 97, 123 are closely adjacent each other (in the extended positions of the components 1, 2 as shown in FIG. 5), the forces which are transmitted from the femur to the tibia and/or in the opposite direction are caused to pass through or close to the axis 12 of the hinge which enhances the stability of the prosthesis in extended positions of the components 1 and 2. This, in turn, enables the wearer of the prosthesis to stand up and remain in upright position for long periods of time without being concerned with the stability of the prosthesis and of the limb in which the prosthesis is implanted.

(3) The pivot axis 12 is spaced apart from the surfaces 14 of the extensions 25, 26, i.e., the pivot axis is located at a level above such surfaces when the patient wearing the prosthesis is standing so that the components 1 and 2 assume the positions which are shown in FIG. 5. The same holds true when the femoral component 2 is caused to pivot between the positions of FIGS. 5 and 6. In other words, the locations of sliding contact between the components 1 and 2 are disposed at a level beneath the pivot axis 12 which, in turn, further enhances satisfactory transfer of forces between the femur and the tibia in actual use of the prosthesis. The extensions or wings 25, 26 can be said to constitute lateral stabilizing or balancing parts which assist in, or effect, the transmission of forces between the femur and the tibia. In addition, the configuration of the extensions 25, 26 is such that they permit certain lateral movements of the femur relative to the tibia and/or vice versa without unduly stressing the main parts 8, 9 and 33 of the hinge. Thus, there is no reason for undesirable material flow in the main parts of the hinge. Such material flow could entail a softening of the material of the housing 6 and/or flange 33 with attendant destruction of the hinge and of the entire prosthesis. The positioning of pivot axis 12 at a level above the surfaces 14, 14, 38 of contact between the femoral component 2 and the tibial component 1 ensures optimal propping of the femur and of the respective component 2. This, in turn, reduces the likelihood of pitching movement in spite of the relative shortness of the pintle 5. A relatively short pintle is desirable because this reduces the need for pronounced resection in order to accommodate the components 1 and 2 in the respective bones.

The aforediscussed features and advantages of the improved prosthesis ensure that the movements of a patient wearing the prosthesis do not appreciably deviate from movements of a person with natural knee joints. This is desirable and advantageous for psychological reasons and on the additional ground that the shanks 3, 4 are less likely to become loose in the respective bones. Moreover, the bones are not subjected to pronounced stresses because the transfer of forces between the femur and the tibia takes place in a manner at least resembling that between a tibia and a femur which are connected to each other by a natural knee joint.

The feature that the planes 97 and 123 are at least substantially parallel to each other in the extended position of the femoral component 2 (FIG. 5) also contributes to greater stability of the prosthesis. Such stability is further enhanced due to the fact that the plane 123 then intersects the shank 3 of the tibial component 1, These two features are particularly important and advantageous when the patient is standing so that the shank 4 is at least substantially in line with the shank 3. It has been found that the aforediscussed positioning and orientation of the planes 97 and 123 relative to each other in the extended position of the femur ensure highly predictable and advantageous transfer of forces between the femur and the tibia.

The selection of a relatively small (fourth) distance (preferably within the range of 0.5 to 4 mm) 122 between the planes 97, 123 in the extended position of the femoral component 2 contributes to convenience of pivoting of the components 1, 2 relative to each other. Still further, such selection of the distance 122 also contributes to more satisfactory transfer of forces between the femur and the tibia of the wearer of the improved prosthesis. This enhances the stability of the prosthesis and hence of the patient when the patient is standing so that the components 1, 2 are held in the positions which are shown in FIG. 5. Experiments indicate that an optimal distance 122 is between about 1.5 mm and about 2.5 mm, As already mentioned above, the first distance 13 is preferably between 16 and 21 mm. The second distance 121 is preferably between 14 and 19 mm. These distances are desirable and advantageous because a thus designed prosthesis ensures highly satisfactory transfer of forces between the components 1, 2 (and hence between the respective bones) in each position of inclination of the component 2 relative to the component 1 and/or vice versa. Moreover, this contributes to the aforediscussed advantage that the prosthesis is not likely to pinch and/or otherwise adversely affect or injure soft tissue within the arc 111 Of FIG. 6, i.e., adjacent the rear portions 113, 112 of the components 1 and 2. Experiments indicate that the aforediscussed distances 13 (between approximately 16 and 21 mm) and 121 (between approximately 14 and 19 mm) are highly satisfactory (or at least quite acceptable) for a large majority of patients who require prostheses of the type shown in FIGS. 1-6 and/or similar prostheses.

The (third) distance 15 (between approximately 20 and 24 mm) is also highly satisfactory for a large number of patients. In other words, such distance is satisfactory for a majority of anatomies which renders it possible to limit the resection of affected bones to a minimum. Moreover, the aforementioned range of distances 15 renders it possible to provide ample room for the transfer of forces between the surfaces 14 of the extensions 25, 26 and the bearing surface 38 of the shell 37 on the base 35, i.e., on the tibial component 1. Still further, the aforediscussed range of distances 15 renders it possible to ensure satisfactory implantation of optimally shaped and dimensioned shanks 3, 4 in the respective bones. Again, this can be carried out with a minimum of resection of the femur and/or tibia.

The thickness of the walls 8, 9 of the housing 6 on the femoral component 2 is selected with a view to ensure that these walls can resist bending stresses when the aforediscussed distances (particularly the vertical distance 15) are within the previously given ranges. It has been found that, at least in most instances, relatively thin walls 8, 9 are capable of resisting the developing bending stresses if the distance 15 is between 20 and 24 mm. In fact, the distance 15 within a range of 20-24 mm even exerts a beneficial influence upon the selection of dimensions of the femoral shank 4, i.e., the transverse dimensions of this shank can be a small or minute fraction of its length without affecting its ability to withstand the developing bending stresses and to successfully resist permanent deformation subsequent to implantation into the femur of a patient.

Though the extensions 25, 26 of the walls 8, 9 constitute optional features of the improved prosthesis, they contribute significantly to its ability to effectively resist all types of stresses which develop in actual use. The extensions 25, 26 are particularly advantageous in the improved prosthesis, i.e., in a prosthesis wherein the pivot axis 12 of the hinge is located at fixed distances from the shanks 3 and 4 and the hinge does not permit longitudinal movements of the shank 3 and/or 4 toward or away from the other shank. Thus, the surfaces 14 of the extensions 25, 26 are in, or can be moved into, large-area contact with the surface 38 of the bearing shell 37 to thus oppose forces which tend to tilt the housing 6 relative to the flange 33 of the hinge and/or vice versa. In this manner, the extensions 25, 26 reduce the likelihood of loosening of the shanks 3, 4 in the respective bones as well as the likelihood of separation of parts of the hinge from the adjacent portions of the bones.

It has been found that a combination of a vertical distance 15 in the range of 23 mm and a horizontal distance 13 in the range of 16 mm constitutes a highly satisfactory compromise which prevents undue stressing of tissue around the prosthesis and, at the same time, enhances the stability of the bones by reducing the likelihood of excessive stressing of the femur and/or tibia. If the horizontal distance 13 is increased well beyond the aforementioned presently preferred range, implantation of the component 1 and/or 2 is much more complex and the magnitude of stresses which are applied to the surfaces 14, 14 and 38 is increased. On the other hand, if the distance 13 is reduced to less than 16 mm, implantation of the prosthesis necessitates a more pronounced resection in order to properly anchor the shanks 3, 4 in the respective bones.

The aforediscussed distances contribute to a pronounced reduction of stresses upon the femoropatellar joint, particularly in comparison with heretofore known prostheses, because the improved prosthesis operates without any forward shifting in the region of the femoral condyle. Shifting in the region of the femoral condyle constitutes a non-physiological stressing of the endoprosthesis. Moreover, the improved prosthesis is capable of functioning not unlike a natural (healthy) knee joint.

Figure 22:
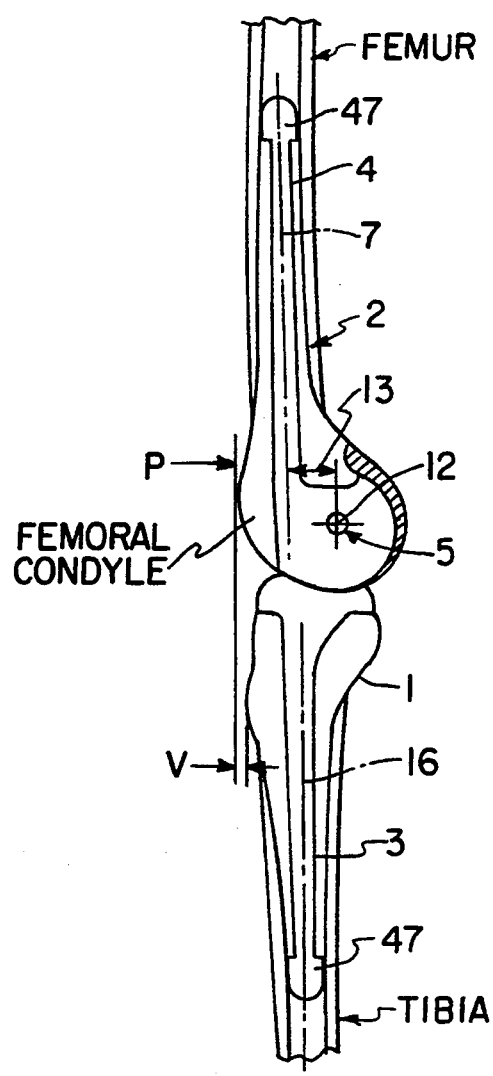
FIG. 22 is a view similar to that of FIG. 5 but further showing the tibial and femoral components in implanted condition behind the patella.

FIG. 22 shows the improved prosthesis in implanted condition. It will be seen that a larger bone resection is necessary in the dorsal region of the femoral condyle if the distance 13 is reduced. This ensures undisturbed articulation (rolling) of the femoral condyle relative to the adjacent upper end portion of the tibia. Resection in the ventral region of the femoral condyle can be avoided by retaining the natural femoropatellar joint.

The patella is embedded between the quadriceps extensor muscle and the patellar ligament and takes up forces P during bending of the knee joint. If the horizontal distance is increased, this entails an increase of the non-physiological spacing V and contributes to an increase of the force P. Resection at the ventral side of the femoral condyle can be avoided or minimized by retaining the natural femoropatellar joint. This reduces the need for replacement of the knee joint prosthesis, i.e., replacement of the knee joint is limited to situations which necessitate corrective operations.

FIG. 22 further shows that each of the shanks 3 and 4 can be provided with a centering means 47 at its free end, i.e., at that end which is remote from the patella. The relative angular positions of the tibial and femoral components 1 and 2 which are illustrated in FIG. 22 correspond to those which are shown in FIG. 5. The length of the shank 3 which is shown in FIG. 22 equals or approximates the length of the shank 4. Furthermore, the centering means at the upper end of the shank 4 is or can be identical with the centering means at the lower end of the shank 3.

Figure 14:
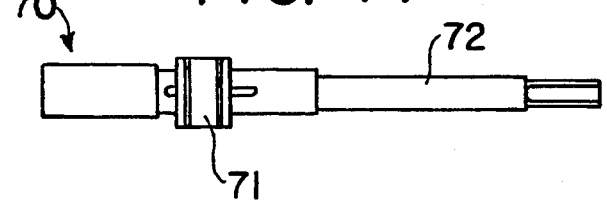
FIG. 14 is an enlarged elevational view of a drilling tool of the type shown in FIG. 10.
Figure 15:
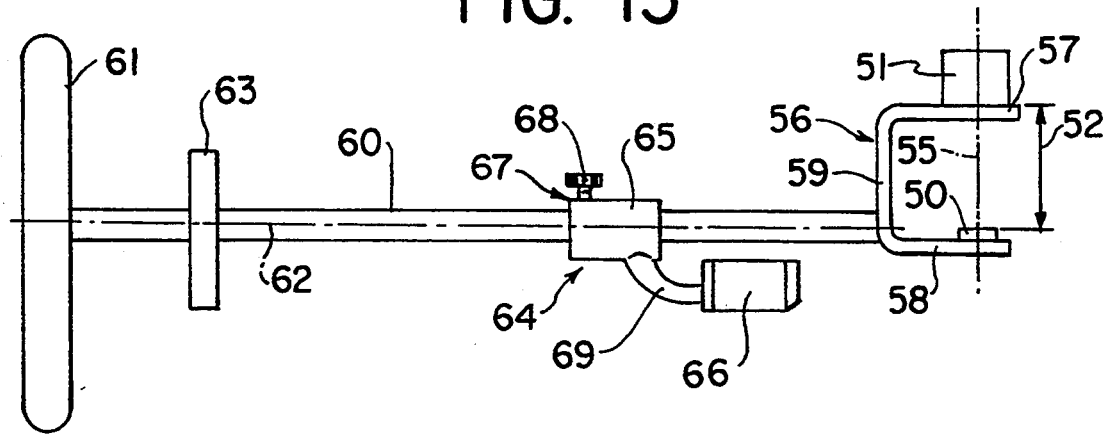
FIG. 15 is an enlarged view of the apparatus which is shown in FIGS. 8 to 10.

FIGS. 8, 9, 10 and 15 illustrate a presently preferred apparatus for making holes or bores in selected portions of bones, e.g., for making a hole in a femur to permit introduction of the pintle 5 of FIG. 3 through such hole in the femur and thereupon through the hole 31 of the bearing element 28, through the opening 34 of the flange 33 and into the blind hole 29 of the bearing element 27. The apparatus comprises a disc-shaped or washer-like locating member 50, and a tubular guide member 51 which is coaxial with and is spaced apart from the locating member 50 (the common axis is shown at 55) a distance (shown at 52) which suffices to permit the positioning of a selected portion of a bone to be drilled between the members 50 and 51. The member 50 can have a cylindrical peripheral surface, the same as the guide member 51 which serves to guide the working end of a drilling tool 70 connected to a handle or shank 72 by a separable coupling 71 (see FIG. 14). The diameter of the locating member 50 can match the diameter 32 of the hole 31 in the bearing element 28, i.e., the locating member 50 can be introduced into the hole 31 from within the housing 6 and the guide member 51 is then outwardly adjacent the selected portion of the bone to be provided with a hole or bore. The preferably cup-shaped rotary drilling tool 70 is then introduced into the guide member 51 and its shank 72 can be rotated by means of a torque transmitting implement or tool 76 of the type shown in FIG. 11 in order to provide the selected portion of the bone with a hole which permits the pintle 5 to enter the hole 31, the opening 34 and the hole 29 to thus complete the coupling of the housing 6 and flange 33 to each other.

The diameter of the locating member 50 need not match the diameter 32 of the hole 31 if the apparatus of FIGS. 8–10 and 15 is furnished with two temporary or spare annular bearing elements or bearings 53, 54 (see FIG. 7) which can be inserted into the sockets 10, 11 of the walls 8, 9 for the sole purpose of permitting proper positioning of the locating member 50 preparatory to making of a hole in that (selected) portion of the bone which is then located between the properly positioned locating member 50 and the guide member 51.

The apparatus further comprises a preferably U-shaped distancing element 56 having a first section or leg 58 rigid with the locating member 50, a second section or leg 57 rigid with the guide member 51, and a third section or web 59 which connects the sections or legs 57, 58 to each other and thus establishes the desired distance 52 between the members 50 and 51. The leg 58 extends through the open end of and into the chamber 20 when the locating member 50 is properly positioned in the hole 31 of the bearing element 28 or in the hole of the bearing element 53 or 54, and the sections 57, 59 then cooperate to maintain the guide member 51 in an optimum position for guidance of the drilling tool 70 into the selected portion of a bone (femur) between the members 50 and 51. The removed material is confined in the cupped drilling tool 70 so that it is withdrawn from the freshly formed hole of the bone in the form of a plug as soon as the tool 70 is extracted from the guide member 51.

The apparatus of FIGS. 8–10 and 15 further comprises an elongated rod- or bar-shaped handle or carrier 60 one end portion of which is rigid with one section (59) of the distancing element 56 and the other end portion of which carries a handgrip portion 61, e.g., a wheel or knob which extends transversely of the longitudinal axis 62 of the handle. The illustrated rod-shaped handle 60 is substantially or exactly parallel to the legs 57, 58 of the distancing element 56 and further serves to reciprocably guide a hammer 63 and a support 64. The support 64 includes a preferably tubular follower 65 which surrounds the handle 60, either entirely or in part, and is disposed between the hammer 63 and the distancing element 56. The support 64 further comprises an anvil or filler 66 which is connected to the follower 65 by a suitably configurated arm 69 and is preferably dimensioned in such a way that the combined thickness of the arm 58 and anvil 66 matches the distance between the internal surfaces 98, 99 in the chamber 20 of the housing 6. At such time, the locating member 50 extends into the hole 31 of the bearing element 28 or into the hole of the bearing element 53 or 54 (whichever of these temporary bearing elements is installed in the wall 9 of the housing 6). This reduces the likelihood of damage to the bone and/or to the housing 6 and/or to the apparatus of FIGS. 8–10 and 15 during drilling of a hole into the bone in a direction from the guide member 51 toward the locating member 50 in the bearing element occupying the socket 11 in the wall 9 of the housing 6.

The tubular follower 65 is slidable along the handle 60 (to permit introduction of the anvil 66 into the chamber 20 of the housing 6) upon loosening of a securing means 67 here shown as including a screw 68 or another suitable threaded fastener which can releasably secure the follower 65 (and hence the entire support 64) to a selected portion of the handle 60. If the anvil 66 resists entry into the chamber 20 of a housing 6 after the locating member 50 is already received in the hole of the bearing element 28, 53 or 54, the hammer 63 can be slid along the rod 60 to apply one or more gentle taps or blows to the follower 65 in order to induce the anvil 66 to enter the chamber 20 behind the properly inserted locating member 50.

Figure 13:
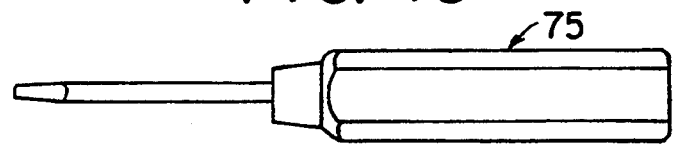
FIG. 13 is an elevational view of a tool which can be used to drive home threaded fasteners into certain parts of the hinge.

FIG. 13 shows a screw driver 75 or a similar readily available tool which can be used to loosen the coupling 71 and/or to turn the screw 68 of the securing means 67.

The apparatus of FIGS. 8–10 and 15 exhibits the advantage that it ensures the removal of a minimal amount of bone material, namely an amount which is just sufficient to permit insertion of the pintle 5 into the housing 6 and flange 33. Another advantage of the improved apparatus is that it can be properly installed, for requisite orientation and guidance of the drilling tool 70, within a very short interval of time which is of great importance to the surgeons in charge of implanting a prosthesis of the type shown in FIGS. 1 to 6. Moreover, the surgeon or surgeons in charge know that the orientation of the tool 70 will be satisfactory on the first try, i.e., that it is not necessary to carry out any corrective drilling into the selected portion of the bone in order to ensure rapid and optimal installation of the pintle 5 in the two leaves of the hinge. Insertion of the locating member 50 into the hole 31 of the bearing element 28 or into the hole of the selected temporary bearing element 53 or 54 invariably ensures proper orientation of the guide member 51, and hence of the drilling tool 70, as long as the locating member 50 is properly retained in the bearing element 28, 53 or 54. This is ensured by employing the anvil 66 in the aforedescribed manner, i.e., to constitute a prop behind the arm 58 for the locating member 50.

The utilization of a drilling tool 70 which is capable of removing a reusable (reinsertable) plug of bone material also constitutes a desirable feature of the improved apparatus. The reinserted plug grows together with the adjacent bone material and thus enhances the stability of the bone.

The improved apparatus is susceptible of many modifications without departing from the spirit of the invention. All that counts is to ensure that the drill 70 and/or the selected portion of the bone cannot perform any stray movements (except possibly in the plane 96) so that the very first attempt results in the making of a drilled hole which is ready to receive the pintle 5 or an analogous shaft serving to articulately connect the housing 6 with the flange 33.

The anvil 66 cooperates with the leg 58 of the distancing element 56 to effectively resist any undesirable stray movements of the guide member 51 relative to the selected portion of the bone to be drilled in response to stresses which are likely to develop while the tool 70 is in the process of removing bone material between the guide member 51 and the locating member 50.

The physician who is in charge of implanting the prosthesis of FIGS. 1 and 2 will first prepare the tibia and the femur for reception and retention of the shanks 3 and 4, respectively. The shanks 3 and 4 are thereupon implanted and secured in optimum positions. At such time, a portion of the femur is outwardly adjacent the wall 9 of the housing 6 which latter is rigid with the femoral component 2. The next step involves insertion of the locating member 50 into the housing 6 through the open end or side of the chamber 20 so that the member 50 enters the hole 31 of the bearing element 28 or the hole of the temporarily inserted bearing element 53 or 54. The anvil 66 is then caused to enter the chamber 20 behind the section or arm 58 for the locating member 50 so that the member 50 is maintained in an optimum position, the same as the guide member 51 which is outwardly adjacent the selected portion of the femur, namely the portion which is outwardly adjacent the wall 9 of the housing 6. The hammer 63 is put to use to gently drive the anvil 66 into the chamber 20 behind the arm 58 if the anvil 66 cannot be advanced into the housing 6 without the application of blows or taps to the tubular follower 65 of the support 64. The support 64 is then fixed in the optimum position of the anvil 66 by tightening the screw 68, and the apparatus of FIGS. 8–10 and 15 is ready to guide the drilling tool 70 toward and into the selected portion of the femur. At such time, the common axis 55 of the members 50, 51 coincides with the pivot axis 12.

When the drilling tool 70 is withdrawn from the guide member 51, it entrains the removed plug of bone material and thus provides room for introduction of the pintle 5 in a manner as described with reference to FIG. 3. The pintle 5 is separably connected with the tool 74 of FIG. 12 in that the externally threaded working end 73 of the tool enters the axial blind bore 42 of the pintle, and the tool 74 is manipulated to introduce the pintle through the freshly formed hole of the femur and into the openings 31, 29 of the bearing elements 28, 27 as well as through the opening 34 of the flange 33 which, at that time, is located in the chamber 20 of the housing 6. The removed bone plug is then withdrawn from the axial recess of the drilling tool 70 and is reinserted into the hole of the femur to enhance the strength of such bone.

Insertion of the pintle 5 into the holes 31, 29 is preceded by introduction of the flange 33 into the chamber 20 of the housing 6, i.e., the components 1 and 2 are moved to the positions of FIG. 5 or 6. This establishes the required circumstances for insertion of the pintle 5 which is thereupon non-rotatably secured to the flange 33 by means of the grub screw 46. If desired or necessary, insertion of the pintle 5 can be preceded by insertion of a pattern whose dimensions match those of the pintle 5 and which is inserted for the purpose of testing the condition of the prosthesis, i.e., whether or not all parts are properly assembled and whether or not the components 1 and 2 are free to pivot relative to each other within the prescribed limits. Any adjustments (if necessary) can be carried out while the housing 6 and the flange 33 are pivotally connected to each other by the aforementioned pattern which is a replica of the pintle 5. The pattern is removed when the person in charge ascertains that all parts of the prosthesis are properly assembled, and the pintle 5 is inserted with assistance from the tool 74. The screw driver 75 of FIG. 13 can be used to apply the grub screw 46.

Figure 11:
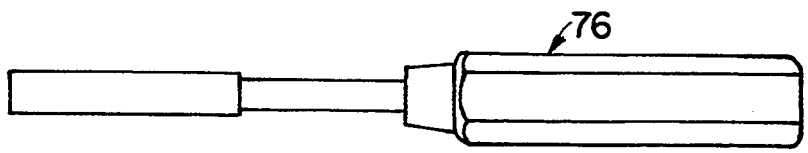
FIG. 11 is an elevational view of an implement which can be used to apply torque to the drilling tool of FIG. 10.

The torque transmitting tool 76 of FIG. 11 can be used to rotate the drilling tool 70 and/or any other tools which must be rotated with the exertion of a reasonable force in the course of an implanting operation.

Figure 20:
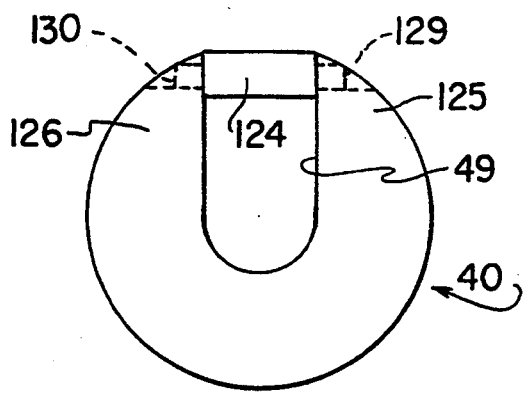
FIG. 20 is a side elevational view of a flange which is similar to that shown in FIG. 17.
Figure 21:
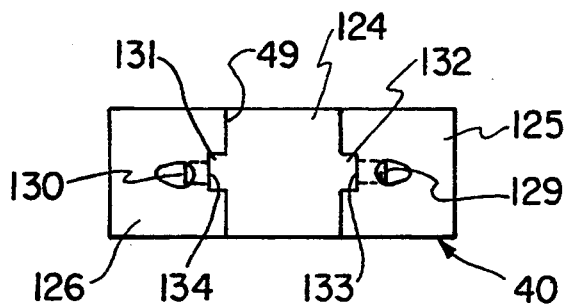
FIG. 21 is a plan view of the flange which is illustrated in FIG. 20.

FIGS. 16 and 17 show that the flange 33 of FIG. 2 (i.e., a flange which resembles or constitutes an eyelet) can be replaced with a substantially U-shaped flange 40 having a slot 49 with an open end which can be closed by a bolt 124 (FIGS. 20 and 21). Such flange is preferred when the designer of the prosthesis desires to non-rotatably mount the pintle 5 in the housing 6 rather than in the flange or in the housing and in the flange. The open end of the slot 49 faces toward the femoral component 2. An advantage of the slot 49 is that the flange 40 of FIG. 17 can be introduced into the housing 6 subsequent to installation of the pintle 5 in the housing, i.e., it is not necessary to introduce the pintle axially through a flange which, at such time, must already fill or nearly fill the chamber of the housing in order to be properly aligned with the holes or openings of the bearing elements. Such design of the flange (40) renders it possible to dispense with the drilling of the aforementioned hole 41 and/or of any tapped hole(s) or bore(s) 42 in the pintle. Still further, it is not necessary to make a hole or bore in the femur because the pintle 5 need not be inserted axially of the holes 29, 31 subsequent to implantation of the shank 4 into the femur of a patient.

Figure 18:
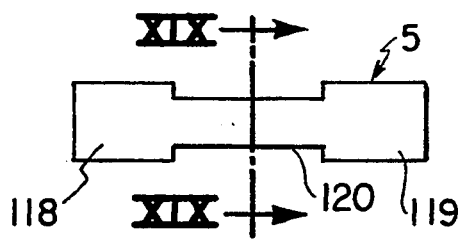
FIG. 18 is an elevational view of a modified pintle.
Figure 19:
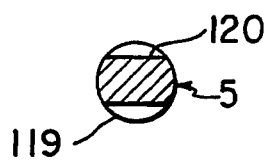
FIG. 19 is a sectional view substantially as seen in the direction of arrows from the line XIX—XIX in FIG. 18.

The pintle 5 is provided with at least one peripheral cutout or recess 120 (see also FIGS. 18 and 19) and with a flat bottom surface in each cutout or recess. The dimensions of the recessed portion of the pintle 5 of FIGS. 17 to 19 are such that, when the end portions 118,119 of the pintle are frictionally installed in the respective bearing elements 27, 28 (i.e., in the housing 6), the slot 49 can receive the median portion of the pintle only when the femoral component 2 is held in the inclined position of FIG. 6. The flange 40 is then slipped onto the median portion of the pintle 5, and the open end of the slot 49 is closed by a transversely extending grub screw or by another suitable blocking or arresting device which prevents accidental extraction of the flange 40 from the housing 6.

FIGS. 20 and 21 show that the open end of the slot 49 can be closed by a bolt 124 which extends transversely of and between the free ends of the legs 125, 126 of the substantially U-shaped flange 40. The bolt 124 is fitted into the open end of the slot 49 and is fixed in such position by two grub screws 129,130 which are driven into tapped bores in the free ends of the respective legs 125, 126.

FIG. 21 shows that the inner sides of the legs 125, 126 can be provided with guide grooves 133, 134 for the complementary end portions or tongues 131, 132 of the bolt 124. The grooves 133, 134 are accessible for insertion of the tongues 131, 132 when the femoral component 2 is pivoted to the position of FIG. 6. When the femoral component 2 is thereupon pivoted to the position of FIG. 5, the open end of the slot 49 is concealed in that the slot extends at a suitable angle in a direction away from the rear end portions 83 of the extensions 25, 26.

The prosthesis of FIGS. 16–21 is particularly desirable and advantageous when the muscles and tendons in the region of the knee joint are healthy so that one should avoid exposure of a selected portion of the femur and/or tibia for the purpose of drilling a hole which is necessary to insert a pintle 5 of the type shown in FIG. 3, i.e., a pintle which must be caused to pass through a hole in the adjacent bone in order to enter the holes 29, 31 and the opening 34.

Knee joint prostheses which are somewhat similar to the prosthesis of the present invention are disclosed in commonly owned U.S. Pats. Nos. 4,538,305, 4,790,853 and 5,026,399.

Without further analysis, the foregoing will so fully reveal the gist of the present invention that others can, by applying current knowledge, readily adapt it for various applications without omitting features that, from the standpoint of prior art, fairly constitute essential characteristics of the generic and specific aspects of our contribution to the art and, therefore, such adaptations should and are intended to be comprehended within the meaning and range of equivalence of the appended claims.

What is claimed is:

1. A knee joint prosthesis comprising a tibial component having a first shank positioned to be directly secured in a tibia; a femoral component having a second shank for direct implantation in a femur; and a hinge connecting said components for relative angular movement between extended first and flexed second positions about a predetermined axis in a predetermined plane extending substantially at right angles to said predetermined axis, said predetermined axis being fixed against movement relative to both of said shanks longitudinally of said shanks, and the shank of said tibial and femoral components respectively defining second and third longitudinal axes respectively located in second and third planes which are substantially perpendicular to said predetermined plane and, in said first positions, are substantially parallel to one another and to a fourth plane including said predetermined axis, said third and fourth planes being spaced apart a first distance and said second and fourth planes being spaced apart a second distance less than said first distance in the first positions of said components, said hinge including first and second leaves which are respectively movable with said tibial and femoral components, and said leaves being arranged to contact each other at a fifth plane which is spaced apart a third distance from a sixth plane including said predetermined axis and being normal to said fourth plane, said second and third planes being spaced apart a fourth distance less than either of said first and second distances.

2. The prosthesis of claim 1, wherein said fifth plane is substantially tangential to a line disposed in a seventh plane of contact between said components, said line being normal to said predetermined plane.

3. The prosthesis of claim 1, wherein said second and third planes define in said second positions of said components an angle which has an apex and said femoral component has a rear portion which is located at said apex in the second positions of said components.

4. The prosthesis of claim 1, wherein said third plane crosses said first shank in the first positions of said components.

5. The prosthesis of claim 1, wherein said fourth distance is between approximately 0.5 and 4 mm in the first positions of said components.

6. The prosthesis of claim 5, wherein said fourth distance is between 1.5 and 2.5 mm.

7. The prosthesis of claim 1, wherein said first distance is between approximately 16 and 21 mm.

8. The prosthesis of claim 7, wherein said first distance is approximately 16 mm.

9. The prosthesis of claim 1, wherein said third distance is between approximately 20 and 24 mm.

10. The prosthesis of claim 9, wherein said third distance is approximately 21 mm.

11. The prosthesis of claim 1, wherein at least one of said shanks is elongated and has a predetermined length and a maximum transverse dimension which is a small fraction of said predetermined length.

12. The prosthesis of claim 1, wherein at least one of said shanks tapers in a direction away from said hinge and the other of said shanks.

13. The prosthesis of claim 1, wherein at least one of said shanks is devoid of undercut portions.

14. The prosthesis of claim 1, wherein at least one of said shanks has an end portion remote from said hinge and provided with means for centering the at least one shank in a bone of a patient.

15. The prosthesis of claim 14, wherein said centering means is substantially star shaped.

16. The prosthesis of claim 14, wherein at least a portion of said centering means consists of a plastic material.

17. The prosthesis of claim 1, wherein at least one of said shanks has a polygonal cross-sectional outline.

18. The prosthesis of claim 17, wherein said at least one shank has a substantially square cross-sectional outline with rounded edges.

19. The prosthesis of claim 1, wherein one of said leaves includes a housing having two spaced apart walls extending from the respective shank toward the component which is movable with the other of said leaves.

20. The prosthesis of claim 19, wherein said hinge further comprises an annular bearing element at each of said walls and a pintle which defines said predetermined axis and extends into said bearing elements.

21. The prosthesis of claim 20, wherein one of said bearing elements has a blind hole for an end portion of said pintle.

22. The prosthesis of claim 21, wherein the other of said bearing elements has a through hole for said pintle, said through hole being coaxial with said blind hole.

23. The prosthesis of claim 20, wherein at least one of said bearing elements consists of a plastic material.

24. The prosthesis of claim 20, wherein said walls have sockets for the respective bearing elements.

25. The prosthesis of claim 20, wherein said housing has a chamber and said walls have confronting surfaces adjacent said chamber, said surfaces having sockets for the respective bearing elements and said bearing elements having surfaces which are flush with the surfaces of the respective walls.

26. The prosthesis of claim 25, wherein said bearing elements have rims in the respective sockets.

27. The prosthesis of claim 19, wherein said housing has a chamber between said walls, said walls having outer sides facing away from said chamber and provided with extensions having arcuate surfaces facing the component which is movable with the other of said leaves.

28. The prosthesis of claim 27, wherein the component which is movable with the other of said leaves has a surface which contacts said extensions.

29. The prosthesis of claim 27, wherein each of said extensions has a pronounced width in the direction of said predetermined axis and said arcuate surfaces are closely adjacent a bearing surface of the component which is movable with the other of said leaves.

30. The prosthesis of claim 29, wherein said housing has a second width which is approximately twice said pronounced width.

31. The prosthesis of claim 27, wherein each of said arcuate surfaces is a convex surface and said extensions have edge faces remote from the respective walls, each of said convex surfaces extending from one of said walls to the edge face of the respective extension, the component which is movable with said other leaf having end faces which are congruent with the edge faces of said extensions.

32. The prosthesis of claim 27, wherein said housing is movable with said femoral component and said extensions extend substantially concentrically with said predetermined axis along arcs of approximately 180°.

33. The prosthesis of claim 32, wherein said femoral component has a side confronting said tibial component and said arcuate surfaces are located at said side of said femoral component.

34. The prosthesis of claim 33, wherein said housing is provided on said femoral component and said femoral component has a rear portion, each of said extensions having an end portion at the rear portion of said femoral component, said side of said femoral component crossing said sixth plane at said rear portion.

35. The prosthesis of claim 34, wherein said sixth plane is a horizontal plane in implanted condition of said components and said end portions of said extensions are located at a level slightly above said horizontal plane.

36. The prosthesis of claim 27, wherein each of said extensions has a front end portion and a rear end portion and extends about said predetermined axis along an arc from the respective rear end portion to the respective front end portion at a front face of said femoral component, said front face being located opposite a rear portion of said femoral component.

37. The prosthesis of claim 36, wherein the front end portions of said extensions are spaced apart from said sixth plane a first predetermined distance in a direction toward said tibial component and said rear end portions are spaced apart from said sixth plane a second predetermined distance in a direction away from said tibial component, said second predetermined distance at least approximating said first predetermined distance.

38. The prosthesis of claim 36, wherein said arc has sections of different curvature.

39. The prosthesis of claim 38, wherein said sections include sections of less pronounced curvature at the end portions of said extensions and at least one section of more pronounced curvature between said end portions.

40. The prosthesis of claim 27, wherein said extensions have front end portions and said one leaf further comprises an arcuate bridge connecting said front end portions.

41. The prosthesis of claim 40, wherein said housing is provided on said femoral component and has a front surface at said bridge, said tibial component having a protuberance adjacent and substantially complementary to said bridge.

42. The prosthesis of claim 19, wherein said housing has a chamber between said walls and said other leaf comprises a flange.

43. The prosthesis of claim 42, wherein said flange at least substantially fills said chamber.

44. The prosthesis of claim 42, wherein said flange has an opening and said hinge further comprises a pintle having end portions received in said housing and a median portion in said opening.

45. The prosthesis of claim 44, wherein said flange has two lateral surfaces which are substantially parallel to each other and are disposed at opposite sides of said predetermined plane.

46. The prosthesis of claim 45, wherein said housing has internal surfaces parallel and adjacent to said lateral surfaces, said lateral surfaces being substantially equidistant from said predetermined plane.

47. The prosthesis of claim 46, wherein said chamber has a substantially rectangular cross-sectional outline in a plane which is normal to said predetermined plane and said internal surfaces flank said chamber, said chamber being further bounded by a surface provided on said housing and substantially parallel to said second plane in the first positions of said components and said chamber being open opposite said last named surface.

48. The prosthesis of claim 42, wherein said other leaf further comprises a base which is substantially normal to said second axis, said flange being disposed substantially centrally of said base.

49. The prosthesis of claim 48, wherein said flange comprises an eyelet.

50. The prosthesis of claim 49, wherein said eyelet has a circular opening for a pintle forming part of said hinge and defining said predetermined axis, said eyelet further having a convex external surface with a center of curvature on said predetermined axis.

51. The prosthesis of claim 48, wherein said other leaf further comprises a bearing shell provided on said base, said base being provided on said tibial component and said flange extending through said shell in a direction toward said femoral component.

52. The prosthesis of claim 51, wherein said shell is U-shaped and includes two legs flanking said flange and a web connecting said legs to each other at a front side of said base.

53. The prosthesis of claim 52, wherein said base has a rear side and said flange is adjacent said rear side.

54. The prosthesis of claim 51, wherein said shell has a bearing surface confronting said femoral component and engageable by extensions of said housing.

55. The prosthesis of claim 54, wherein said bearing surface extends from a front side toward a rear side of said base.

56. The prosthesis of claim 54, wherein said extensions have front end portions engageable with a front portion of said bearing surface, said bearing surface further having a substantially plane rear portion and said front portion extending beyond said rear portion in a direction toward said femoral component.

57. The prosthesis of claim 56, wherein said rear portion of said bearing surface is contacted by said extensions at least in the second positions of said components.

58. The prosthesis of claim 54, wherein said extensions have sliding surfaces arranged to contact said bearing surface.

59. The prosthesis of claim 54, wherein at least one of said extensions engages said bearing surface in response to the application of a force which urges said components toward each other.

60. The prosthesis of claim 54, wherein said bearing surface includes a substantially plane rear portion, a front portion extending beyond said rear portion toward said femoral component and a concave intermediate portion having a steep front part adjacent said front portion.

61. The prosthesis of claim 54, wherein said bearing surface includes recessed guide portions for said extensions.

62. The prosthesis of claim 51, wherein said shell consists of a plastic material.

63. The prosthesis of claim 42, wherein said flange has an opening and said hinge further comprises a pintle which extends through said opening, said pintle having end portions installed in annular bearing elements provided therefor in said housing.

64. The prosthesis of claim 63, wherein said hinge further comprises means for non-rotatably securing said pintle to said flange.

65. The prosthesis of claim 64, wherein said securing means includes a grub screw.

66. The prosthesis of claim 63, wherein said pintle has an end face provided with an axially extending recess for a working end of a tool which facilitates insertion of said pintle into said housing and said flange.

67. The prosthesis of claim 63, wherein said pintle consists, at least in part, of a metallic material.

68. The prosthesis of claim 63, wherein said housing has sockets for said bearing elements and said bearing elements consist of a plastic material, said pintle being rotatable in said bearing elements.

69. The prosthesis of claim 19, wherein said housing has extensions consisting of a hard metal and engageable with the component which is movable with the other of said leaves.

70. The prosthesis of claim 1, wherein at least one of said components has an elastically deformable shank.

71. The prosthesis of claim 1, wherein said predetermined axis constitutes the sole axis for relative angular movement of said components.

72. A knee joint prosthesis comprising a tibial component having a first shank positioned to be directly secured to a tibia; a femoral component having a second shank for direct implantation in a femur; and a hinge connecting said components for relative angular movement between extended first and flexed second positions about a predetermined axis in a predetermined plane extending substantially at right angles to said predetermined axis, said predetermined axis being fixed against movement relative to both of said shanks longitudinally of said shanks, and the shank said tibial and femoral components respectively defining second and third longitudinal axes respectively located in substantially parallel second and third planes which are substantially perpendicular to said predetermined plane and, in said first positions, are substantially parallel to one another and to a fourth plane including said predetermined axis, said third and fourth planes being spaced apart a first distance of about 16 to 21 mm and said second and fourth planes being spaced apart a second distance less than said first distance in the first positions of said components, and said components being arranged to contact each other at a fifth plane which is spaced apart a third distance of about 20 to 24 mm from a sixth plane including said predetermined axis and being normal to said fourth plane, said second and third planes being spaced apart a fourth distance of about 0.5 to 4 mm, and said fourth distance being less than said second distance.

* * * * *